(12) United States Patent
Daanen

(10) Patent No.: US 8,697,935 B2
(45) Date of Patent: Apr. 15, 2014

(54) METHOD AND SYSTEM FOR ALERTING THE OCCURRENCE OF WETNESS

(75) Inventor: Henricus Adrianus Maria Daanen, Soesterberg (NL)

(73) Assignee: Nederlandse Organisatie Voor Toegepast-Natuurwetenschappelijk Onderzoek TNO, Delft (NL)

( * ) Notice: Subject to any disclaimer, the term of this patent is extended or adjusted under 35 U.S.C. 154(b) by 355 days.

(21) Appl. No.: 12/988,150

(22) PCT Filed: Apr. 16, 2009

(86) PCT No.: PCT/NL2009/050205
§ 371 (c)(1),
(2), (4) Date: Nov. 24, 2010

(87) PCT Pub. No.: WO2009/128719
PCT Pub. Date: Oct. 22, 2009

(65) Prior Publication Data
US 2011/0060302 A1 Mar. 10, 2011

(30) Foreign Application Priority Data

Apr. 16, 2008 (EP) ..................................... 08154613

(51) Int. Cl.
*A61F 13/15* (2006.01)
*A61F 13/20* (2006.01)
(52) U.S. Cl.
USPC ........................................................ 604/361
(58) Field of Classification Search
USPC .................. 604/304–308, 358–402; 600/549; 602/49
See application file for complete search history.

(56) References Cited

U.S. PATENT DOCUMENTS 4,205,672 A * 6/1980 Dvorak ......................... 128/886

2006/0247588 A1 * 11/2006 Olson et al. ................... 604/361
2008/0045913 A1 * 2/2008 Johnson et al. ............... 604/361

FOREIGN PATENT DOCUMENTS

WO    WO 2008/020347 A1    2/2008

OTHER PUBLICATIONS

University of British Columbia Calculus Online Course Notes: Newton's Law of Cooling (Herein "Newton"; Accessed at—http://www.ugrad.math.ubc.ca/coursedoc/math100/notes/diffeqs/cool.html).*
University of British Columbia Calculus Online Course Notes: Newton's Law of Cooling (Archive Copy from Feb. 16, 2007 at—http://archive.org/web/web.php).*
Bouhassira et al., "Investigation of the paradoxical painful sensation ('illusion of pain') produced by a thermal grill", Pain, vol. 114, pp. 160-167, Mar. 2005.

* cited by examiner

*Primary Examiner* — Jackie Ho
*Assistant Examiner* — Peter S Vasat
(74) *Attorney, Agent, or Firm* — Birch, Stewart, Kolasch & Birch, LLP

(57) ABSTRACT

System and method for alerting the occurrence of wetness on a skin area under a cover layer, comprising detection means for detecting the occurrence of wetness on the skin area under the cover layer, exposure means for exposing at least part of the skin area to a temperature having a course which mainly corresponds to the temperature course which would have occurred in the absence of said cover layer, and actuation means for actuating said exposure means under control of said detection means. The exposure means may comprise an electricity source, electricity/temperature conversion means, and control means for controlling the electrical current or voltage in accordance with a predetermined curve which results in an output temperature of the electricity/temperature conversion means which mainly corresponds to the temperature course which would have occurred in the absence of said cover layer. The electricity/temperature conversion means may comprise one or more Peltier elements.

9 Claims, 1 Drawing Sheet

METHOD AND SYSTEM FOR ALERTING THE OCCURRENCE OF WETNESS

BACKGROUND

Articles intended for personal care like diapers, incontinence products etc. are designed to be sufficiently absorbent to pull urine etc. away from the wearer's skin, in order to reduce skin area irritation caused by prolonged wetness exposure. By making the articles highly absorbent, it is difficult for the wearer to realize that an insult of the article has occurred, which might lead to undesired effects for the wearer and/or the wearer's surroundings. It thus may be desirable provide a form of signalling to make the wearer aware that urination has occurred.

WO2008020347 discloses such an article which includes an alerting element providing the wearer to feel a change in temperature against the skin area upon urination, comprising a sensor for urination sensing, which activates a "thermal grill", i.e. a set of geometrically alternate heat and cold exposing elements, e.g. formed by Peltier elements which are alternately energized from a battery to expose heat and cold to the wearer's skin.

SUMMARY

It is an object to provide an alerting function giving a more natural "getting wet" alert using electronic means which cause a sensation of clamminess to the user.

A method is provided that alerts a user of occurrence of wetness on a skin area residing under a cover layer. The method comprises the steps of:
- exposing at least part of the skin area to an electricity/temperature conversion circuit;
- detecting the occurrence of wetness on the skin area under the cover layer;
- responding to detection of wetness by activating the electricity/temperature conversion circuit, and controlling the electrical current or voltage that is applied to the electricity/temperature conversion circuit in accordance with a predetermined time dependent curve, corresponding to exposure of said at least part of the skin area to a time dependent temperature having a temperature course corresponding to wetting of the skin in the absence of said cover layer. A system is also provided, which applies this method. In an embodiment the system may comprise an incontinence product, a wetness detector and temperature exposure means being located on a surface of the incontinence product for application to the skin of the user.

In this way, after detecting—e.g. by means of measuring electrical conductivity—the occurrence of wetness on the skin area under the cover layer, a "wetness sensation" is aroused by means of the exposure to a cold sensation having an intensity course which follows an (e.g. previously recorded or computed) temperature curve as a function of time, which corresponds to the cold sensation (or cold effect) which occurs when a not-covered skin or similar surface is wetted, or when the cover of a initially covered wet skin is removed at a certain moment. In this way a wetness sensation can be simulated by means of temperature control of the exposure means, viz. enabling those means to expose at least part of the skin area to a temperature having a course which mainly corresponds to the temperature course which would have occurred in the absence of said cover layer.

In an embodiment, the function of time provides at least for a gradual initial slope of temperature decay, with a slope that is larger than a temperature slope due to evaporation, if any, of the wetness from the skin area from under the cover layer. This simulates a natural sensation of wetness that can occur, even if this sensation does not correspond to the actual conditions of wetting. An initial slope between fifty and five hundred millidegrees per second may be used for example. Such temperature slopes have been found to occur in practice without cover layer. In a further embodiment a temperature course with an initial exponential decay $Tf+A*\exp(-t/t0)$ with a decay amplitude A of at least one degree centigrade, a decay time t0 in a range between five seconds and fifty seconds and an asymptotic temperature Tf that lies A degrees below a temperature at an initial time point. An initial temperature course approximating this form has been found to occur in practice.

BRIEF DESCRIPTION OF THE DRAWING

These and other object and advantageous aspects will become apparent from a description of an exemplary embodiment of a system, by reference to the following figures

DETAILED DESCRIPTION

Figure 1:
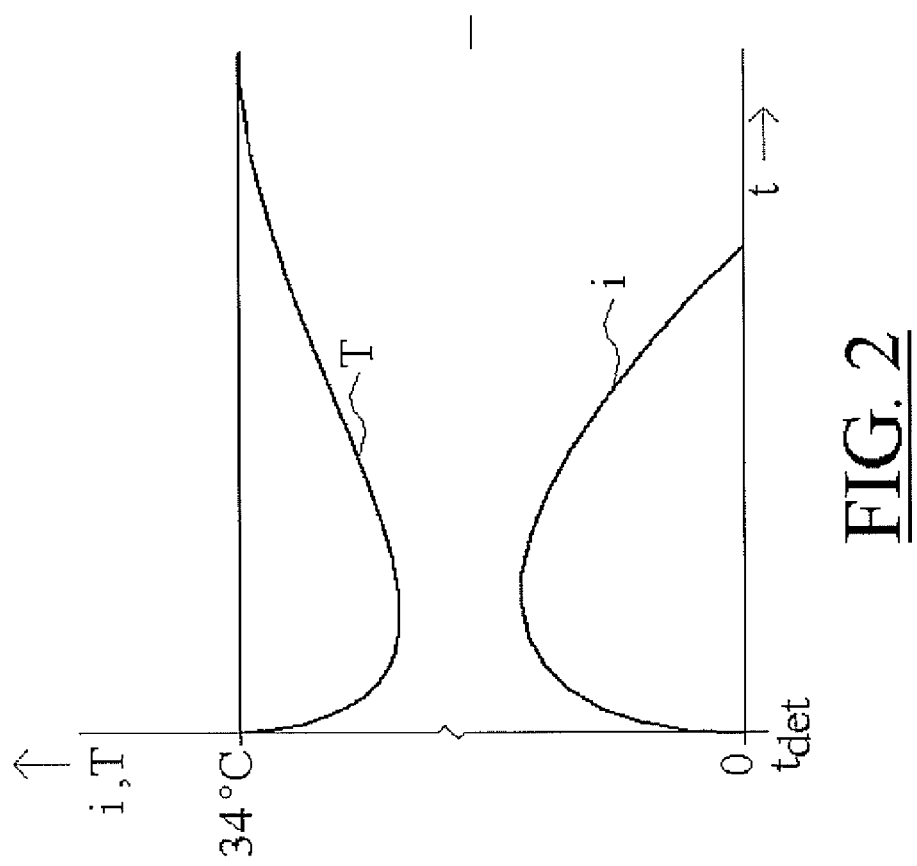
FIG. 1 illustrates an article intended for personal care, comprising means for alerting the occurrence of wetness on the covered skin area.

FIG. 1 shows a system for alerting the occurrence of wetness on a human skin area 1 under a cover layer, i.e. an incontinence product 2. On the side of the skin area 1 the product 2 contains a small and integrated package 3 which comprises a detection module 4 which is enabled to detect the occurrence of clamminess in the skin area 1 under the cover layer 2, caused by e.g. urination. Detection module 4 may comprise an electrical conductivity sensor for example. The package 3, moreover, comprises an exposure module 5 for exposing part of the skin area 1 to a temperature having a course which mainly corresponds to the temperature course which would have occurred in the absence of said cover layer (which will be discussed more in detail hereinafter), and an actuation and control module 6 for actuating said exposure means under control of said detection means. An electricity source, in the form of a small battery 7 is provided for energizing the various modules, including the exposure module 5 which has the form of an electricity/temperature conversion module comprising one or more Peltier elements, and the activation and control module 6. The latter is arranged to be activated by the clamminess detection module 4 and subsequently to control the electrical current in accordance with a curve which has been written into a memory in module 6 previously.

The result is that, as soon as clamminess is detected by module 4, module 6 outputs an electrical current, supplied by the battery 7 to the Peltier module 5 which exposes an temperature fall to the user's skin which corresponds to the temperature course which would have occurred in the absence of said cover layer and which thus simulates that phenomenon and alerts the user, so that the user can take measures.

Figure 2:
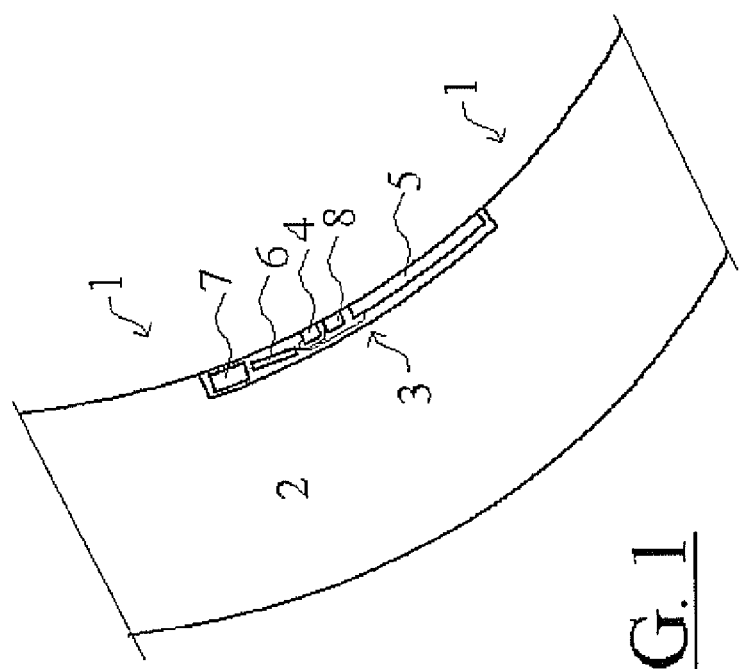
FIG. 2 shows a temperature curve which corresponds to the cold sensation which occurs when a not-covered skin or similar surface is wetted, or when the cover of an initially covered wet skin is removed

FIG. 2 shows a temperature curve which corresponds to the cold sensation which occurs when a not-covered skin or similar surface is wetted, or when the cover of an initially covered wet skin is removed. Additionally a curve is shown of the electric current which—under control of the control module 6—flows through the Peltier module 5. FIG. 2 shows the temperature course T and the current i through the Peltier module 5, causing the T-curve. The T-curve starts from the local skin temperature, e.g. about 34° C., which can be detected by a small temperature sensor 8. The current i causes a cooling effect on the user's skin 1, causing an illusive sensation of clamminess, evaporating in the air, which simulated effect will alert the user that urination occurred. The skin temperature will mostly be between 25 and 35° C. The Peltier module 5 will normally adopt the same temperature as the skin area 1. From the moment that clamminess is detected by detector 4 the Peltier module will start to cool down the skin according to a cooling curve the exact shape of which—in order to give an optimal clamminess sensation to the user—depends on the starting temperature (e.g. 34° C. in FIG. 2).

It has been found that the temperature course of the skin, i.e. temperature as a function of time when the skin is wetted, initially corresponds approximately to an exponential decay $T=T_f+A\exp(-t/t0)$, wherein $T_f$ is an end value for large time values "t", A is the amplitude of the decay and t0 is a decay time. For drops on gauze on the human skin and with a temperature sensor between the gauze and the skin, decay times t0 within a range between 5 and 50 seconds have been found, possibly dependent on drop volume. The decay amplitude A was found to depend approximately linearly on drop volume, with amplitudes within a range between 1 and 5 degrees centigrade for practical drops with volumes in the range of 0.01 and 0.1 milli-liter ($10^{-8}$-$10^{-7}$ $m^3$). The ratio A/t0 of the decay amplitude A and the decay time t0 defines an initial temperature slope. Values of this slope were found to lie within a range between 0.05 and 0.2 degrees centigrade per second.

Once the drop has evaporated, after several minutes (e.g. 5 minutes), the skin was found to warm back to its original temperature. When covered with water impermeable foil, little or no temperature change was observed due to drops on the gauze. But immediately when the foil was removed the exponential temperature drop set in.

As will be clear, the initial perception of wetting through temperature changes is determined entirely by the initial temperature decay. The later temperature rise only affects perception when it sets in, but before that wetting has already been perceived. Therefore, simulation of the initial exponential decay or at least an initial part of it suffices to create the sensory temperature stimulus corresponding to wetting during an initial time interval. For the perception during the initial part of the decay it may even suffice to provide for a temperature change with the slope A/t0 of a natural temperature decay. Preferably the decay is maintained for a time period that is sufficient to result in perceptible temperature change, for example at least one degree centigrade and more preferably at least two degrees centigrade. When an exponential decay is used a decay amplitude A of at least one degree centigrade and more preferably at least two degree centigrade or five centigrade is used in order to ensure that the effect rises above a minimum perception threshold.

Because various decay time t0 can occur for practical drops, any decay time t0 in the observed range may create a temperature effect corresponding to wetting that may be perceived as wetting. For perception of wetting it is not necessary to simulate the effect of the actual quantity of wetting within incontinence product 2, or actual environmental conditions such as drafts. Because various decay amplitudes can occur, dependent on drop volume, any decay amplitude may create a temperature effect corresponding to wetting that may be perceived as wetting.

The system comprises a cover layer, e.g. an incontinence product 2 such as a nappy for children or adults, a detection module 4, an exposure module 5 and an actuation and control module 6. Detection module 4, exposure module 5 and actuation and control module 6 may be integrated in an integrated package. A small battery 7 may be provided for energizing the various modules. Actuation and control module may be a control circuit, such as a microcontroller. Actuation and control module 6 may comprise a memory (not separately shown). Actuation and control module 6 has an input coupled to detection module 4 and an output coupled to exposure module 5.

Detection module 4 is configured to detect the occurrence of clamminess in the skin area 1 under the cover layer 2, i.e. between cover layer 2 and the skin of a subject that wears incontinence product, caused by e.g. urination. Detection module 4 may comprise an electrical conductivity sensor for example, which detects clamminess from a change in conductivity between terminals of the sensor. . . Exposure module 5 is configured to expose a part of a skin area 1 to a time dependent temperature change. Exposure module 5 is an electricity/temperature conversion module comprising one or more Peltier elements. A wetness sensitive part of detection module 4 and an exposure part of exposure module 5 may be located on a skin side surface of incontinence product 2.

Actuation and control module 6 is arranged receive a detection of clamminess from detection module 4 and to respond to the detection by causing a time dependent electrical current or voltage to be applied to exposure module 5. A time dependent electrical current or voltage is used in accordance with a curve that simulates a temperature effect of wetting in the absence of incontinence product 2 at least over an initial time interval.

The time dependence of the electrical current or voltage may provide for an exponential decay of the exposure temperature from exposure module 5 with a decay time of between five and fifty seconds and an amplitude of at least one degree centigrade and more preferably at least two degrees centigrade, for example five degrees centigrade. The time dependence of the electrical current or voltage may be defined by data stored in the memory of actuation and control module 6 for example, actuation and control module 6 controlling exposure module 5 dependent on the stored value. Actuation and control module 6 may comprise a digital to analog converter to convert stored digital values into analog control signals. Digital to analog conversion may be realized by controlling a duty cycle of cooling (a fraction of time that cooling is applied in a periodic pattern with a frequency higher than the decay time) that realizes the values on average. In another embodiment current values for different time points may be computed by actuation and control module 6 when they are needed. In another embodiment, an analog circuit may be used to generate the temperature course, such as an RC filter with an RC time equal to the decay time t0, using an output capacitor that is coupled to a voltage source via a resistor. In this case a flip-flop may be used to realize the voltage source, the flip-flop being set by detection module upon detection of clamminess.

Actuation and control module 6 may use a temperature decay that differs from the exponential decay after some initial time interval without affecting perception during that initial time interval. In embodiment an exponential decay is used at least for an initial time interval with a length of the decay time. Furthermore, it will be appreciated that deviations from exact mathematically exponential decay may be used that are sufficiently small so that they do not affect perception. A linearly slope temperature may be used for example, with a slope A/t0 corresponding to a ratio of the decay amplitude A and the decay time t0, at least during an initial time interval of sufficient length to produce a perceptible temperature change, of at least one degree centigrade for example and more preferably at least two degrees centigrade. A time interval of the length of the decay time t0 may be used for example. A slope from a range between 0.05 and 0.5 degrees centigrade per second may be used for example.

Actuation and control module 6 may provide for a rise in exposure temperature after the initial exponential decay, using time dependence of the electrical voltage to simulate a natural temperature rise that corresponds to the rise without incontinence product 2 after evaporation. However, actuation and control module 6 may use a temperature course at the time of the rise that differs from the natural rise without affecting perception at times before the rise sets in.

The point to be noted is that in each case exposure module 5 is made to expose the skin initially to a gradually decreasing temperature with a temperature slope that is greater than the temperature slope, if any, that is possible due to evaporation from skin under incontinence product 2. The temperature is not changed abruptly, but with a temperature slope that is possible when more evaporation occurs than is allowed by incontinence product 2, up to temperature slopes possible due to evaporation from bare skin.

Finally it is noted that it is preferred that the integrated package 3 is at least partly formed by or on flexible materials, in order to accommodate it to the user's skin shape.

A method has been described for alerting the occurrence of wetness on a skin area (1) residing under a cover layer (2), comprising the steps of
- detect the occurrence of wetness on the skin area under the cover layer;
- activate exposure means for exposing at least part of the skin area to a temperature having a course which mainly corresponds to the temperature course which would have occurred in the absence of said cover layer.

A system for alerting the occurrence of wetness on a skin area (1) under a cover layer (2) has been described that comprises detection means (4) for detecting the occurrence of wetness on the skin area under the cover layer, exposure means (5) for exposing at least part of the skin area to a temperature having a course which mainly corresponds to the temperature course which would have occurred in the absence of said cover layer, and actuation means (6) for actuating said exposure means under control of said detection means. The exposure means of this system may comprise an electricity source (7), electricity/temperature conversion means (5), and control means (6) for controlling the electrical current or voltage in accordance with a predetermined curve which results in an output temperature of the electricity/temperature conversion means which mainly corresponds to the temperature course which would have occurred in the absence of said cover layer. The electricity/temperature conversion means may comprise one or more Peltier elements.

The invention claimed is:

1. A method of providing an alert of occurrence of wetness on a skin area residing under a cover layer, comprising the steps of:
    exposing at least part of the skin area to an electricity/temperature conversion circuit;
    detecting the occurrence of wetness on the skin area under the cover layer;
    responding to detection of wetness by activating the electricity/temperature conversion circuit; and
    controlling the electrical current or voltage that is applied to the electricity/temperature conversion circuit in accordance with a predetermined time dependent curve,
    wherein the predetermined time dependent curve has an initial slope between fifty and five hundred millidegrees temperature decrease per second.

2. A method of providing an alert of occurrence of wetness on a skin area residing under a cover layer, comprising the steps of:
    exposing at least part of the skin area to an electricity/temperature conversion circuit;
    detecting the occurrence of wetness on the skin area under the cover layer;
    responding to detection of wetness by activating the electricity/temperature conversion circuit; and
    controlling the electrical current or voltage that is applied to the electricity/temperature conversion circuit in accordance with a predetermined time dependent curve,
    wherein the predetermined time dependent curve comprises an initial exponential temperature decay according to $Tf+A*\exp(-t/t0)$ with a decay amplitude A of at least one degree centigrade, a decay time t0 in a range between five seconds and fifty seconds and an asymptotic temperature Tf that lies A degrees below a temperature at an initial time point.

3. A system for providing an alert of the occurrence of wetness on a skin area under a cover layer, the system comprising:
    a wetness detector configured to detect the occurrence of wetness on the skin area under the cover layer;
    exposure means comprising electricity/temperature conversion circuit and configured to expose at least part of the skin area to a temperature controlled by the electricity/temperature conversion means; and
    an actuation circuit for controlling an electrical current or voltage applied to the electricity/temperature conversion means, the actuation circuit being configured to apply an electrical current or voltage in accordance with a predetermined time dependent curve,
    wherein the predetermined time dependent curve has an initial slope between fifty and five hundred millidegrees temperature decrease per second.

4. The system according to claim 3, wherein said electricity/temperature conversion circuit comprises one or more Peltier elements.

5. The system according to claim 3, wherein said wetness detector comprises a conductivity sensor.

6. A system for providing an alert of the occurrence of wetness on a skin area under a cover layer, the system comprising
    a wetness detector configured to detect the occurrence of wetness on the skin area under the cover layer;
    exposure means comprising electricity/temperature conversion circuit and configured to expose at least part of the skin area to a temperature controlled by the electricity/temperature conversion means; and
    an actuation circuit for controlling an electrical current or voltage applied to the electricity/temperature conversion means, the actuation circuit being configured to apply an electrical current or voltage in accordance with a predetermined time dependent curve,
    wherein the predetermined time dependent curve comprises an initial exponential temperature decay according to $Tf+A*\exp(-t/t0)$ with a decay amplitude A of at least one degree centigrade, a decay time t0 in a range between five seconds and fifty seconds and an asymptotic temperature Tf that lies A degrees below a temperature at an initial time point.

7. The system according to claim 6, wherein said electricity/temperature conversion circuit comprises one or more Peltier elements.

8. The system according to claim 6, wherein said wetness detector comprises a conductivity sensor.

9. The system according to claim 6, wherein the cover layer is an incontinence product.

\* \* \* \* \*

UNITED STATES PATENT AND TRADEMARK OFFICE
CERTIFICATE OF CORRECTION

PATENT NO.       : 8,697,935 B2
APPLICATION NO. : 12/988150
DATED            : April 15, 2014
INVENTOR(S)      : Henricus Adrianus Maria Daanen It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 439 days.

Signed and Sealed this

Twenty-ninth Day of September, 2015

Michelle K. Lee
*Director of the United States Patent and Trademark Office*